United States Patent
Yamazaki et al.

[11] Patent Number: 5,570,403
[45] Date of Patent: Oct. 29, 1996

[54] X-RAY CT IMAGING APPARATUS WITH VARIED ENERGY LEVEL DETECTION CAPABILITY

[75] Inventors: Masahiko Yamazaki; Yoshiaki Yaoi, both of Tochigiken, Japan

[73] Assignee: Kabushiki Kaisha Toshiba, Kawasaki, Japan

[21] Appl. No.: 229,635

[22] Filed: Apr. 19, 1994

[30] Foreign Application Priority Data

Apr. 19, 1993 [JP] Japan .................................. 5-091319

[51] Int. Cl.$^6$ ........................................................ A61B 6/00
[52] U.S. Cl. ................................................ 378/5; 378/19
[58] Field of Search .................................... 378/5, 19, 84, 378/98.9, 98.11, 98.12

[56] References Cited

U.S. PATENT DOCUMENTS

| | | | |
|---|---|---|---|
| 4,149,080 | 4/1979 | Schittenhelm | 378/19 X |
| 4,247,774 | 1/1981 | Brooks | 378/19 X |
| 4,870,667 | 9/1989 | Brunnett et al. | 378/19 |
| 4,958,363 | 9/1990 | Nelson et al. | 378/85 |
| 4,965,726 | 10/1990 | Heuscher et al. | |
| 5,018,173 | 5/1991 | Komai et al. | 378/98.9 X |
| 5,241,576 | 8/1993 | Lonn | 378/19 |
| 5,400,379 | 3/1995 | Pfoh et al. | 378/19 |

FOREIGN PATENT DOCUMENTS

58-206996  12/1983  Japan ......................... 378/19

*Primary Examiner*—David P. Porta
*Attorney, Agent, or Firm*—Oblon, Spivak, McClelland, Maier & Neustadt, P.C.

[57] ABSTRACT

An X-ray computerized tomographic (CT) imaging apparatus which can achieve a multiple energy scanning system on a real time basis so that plural kinds of tomographic information can be obtained corresponding to plural types of energy characteristics. The X-ray CT imaging apparatus includes: an X-ray tube for irradiating an X-ray to a biological body under medical examination; a plurality of detection systems for detecting an X-ray energy transmitted through the biological body, in which the plural detection systems have different energy characteristics respectively; a data acquisition unit for acquiring respective transmission X-ray energy data of the biological body which are detected by the plural detection systems; and a reconstruction unit for reconstructing a tomographic image for the biological body in accordance with data from the data acquisition unit.

4 Claims, 12 Drawing Sheets

ENERGY
CHARACTERISTIC
MODE 1

ENERGY
CHARACTERISTIC
MODE 2

FIG. 5

X-RAY BEAM
DETECTOR 2
DETECTOR 1

FIG. 6

PATIENT
X-RAY BEAM
DETECTOR 2
DETECTOR 1

X-RAY CT IMAGING APPARATUS WITH VARIED ENERGY LEVEL DETECTION CAPABILITY

BACKGROUND OF THE INVENTION

1. Technical Field

The present invention relates to an X-ray computerized tomographic (CT) imaging apparatus for use with a medical examination.

2. Background Art

In recent years, there has been widely used a CT (computerized tomographic) imaging apparatus where an X-ray is radiated to a biological body under medical examination so that a quantity of transmission X ray is detected. Data are acquired based on the detected transmission X-ray quantity, and a tomographic image of the biological body is reconstructed in accordance with the acquired data.

There is also available a double-slice CT apparatus. In the double-slice CT apparatus, a detector having a fanbeam form is arranged in two rows in the direction of slice (that is in a longitudinal direction) so that the detector can simultaneously acquire two-slice worth data.

Figure 1:
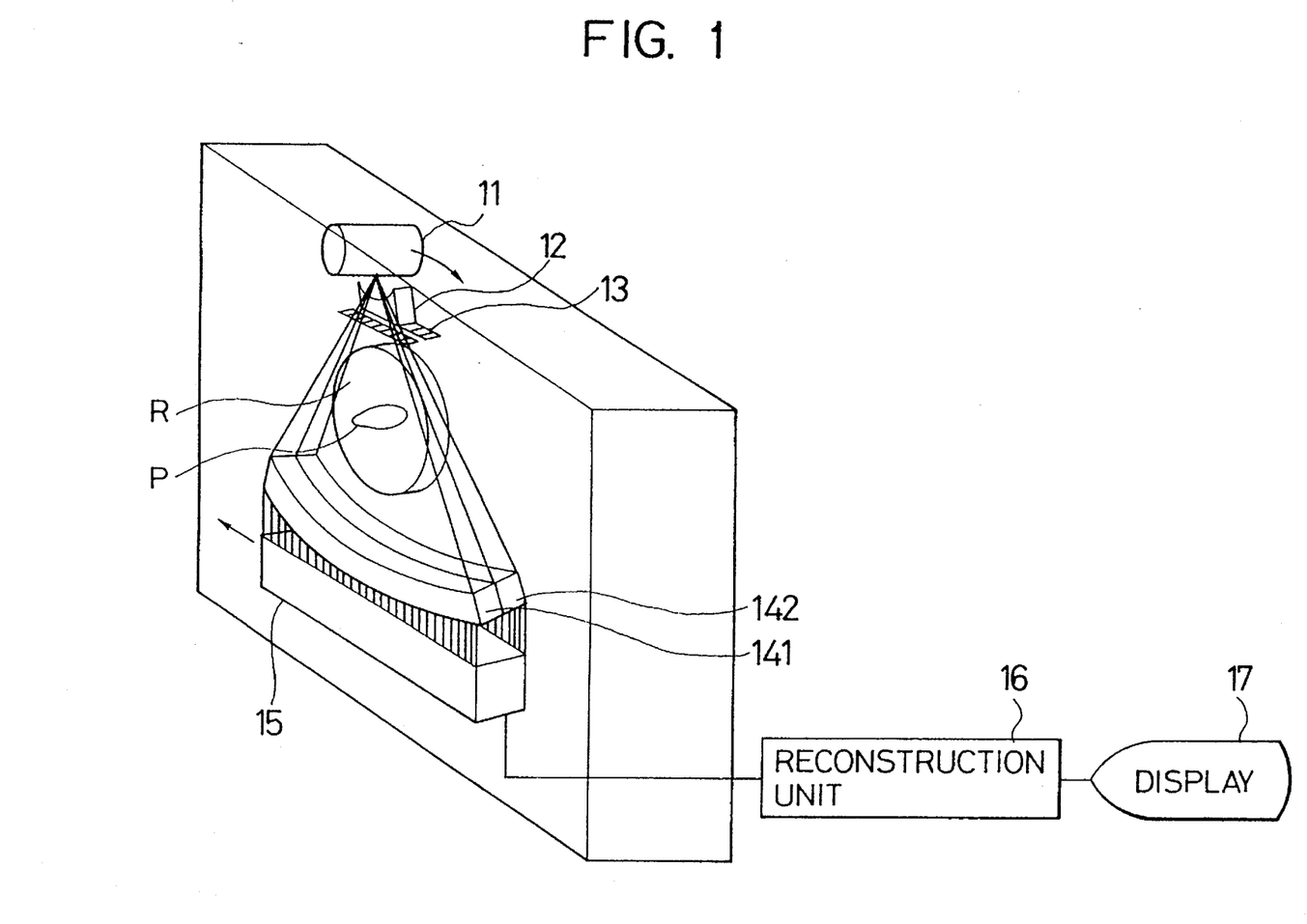
FIG. 1 is a schematic diagram showing the double-slice CT apparatus.

FIG. 1 is a schematic diagram showing the double-slice CT apparatus. Referring to FIG. 1, the double-slice CT apparatus includes an X-ray tube 11 for radiating X-ray to the biological body P placed within an imaging region R, detectors 141, 142 for detecting transmission X-ray quantity of the biological body P, a data acquisition unit 15 for acquiring data based on the transmission X-ray quantity detected by the detectors 141, 142, an image reconstruction unit 16 for reconstructing the tomographic image of the biological body P in accordance with the data from the data acquisition unit 15, and a display unit 17 for displaying a reconstructed tomographic image. Referring still to FIG. 1, there are also provided a wedge 12 and a slit 13, located in a close vicinity of the X-ray tube 11 and in a direction toward the detectors 141, 142, so that X-ray is uniformly exposed to the detectors 141, 142 regardless of irradiating angles, by controlling quality and dosage of the exposure X-ray.

Moreover, there is available a double-slice apparatus employed in a helical scanning system. In such a helical scanning system, a couch on which a patient is laid is continuously translated along a longitudinal direction, while X-ray beams are continuously exposed to the patient. Then, acquired are data concerning the transmission X-ray quantity from the detector and a translated amount of the couch. In accordance with the data, the tomographic images for the patient are reconstructed.

Figure 2A:
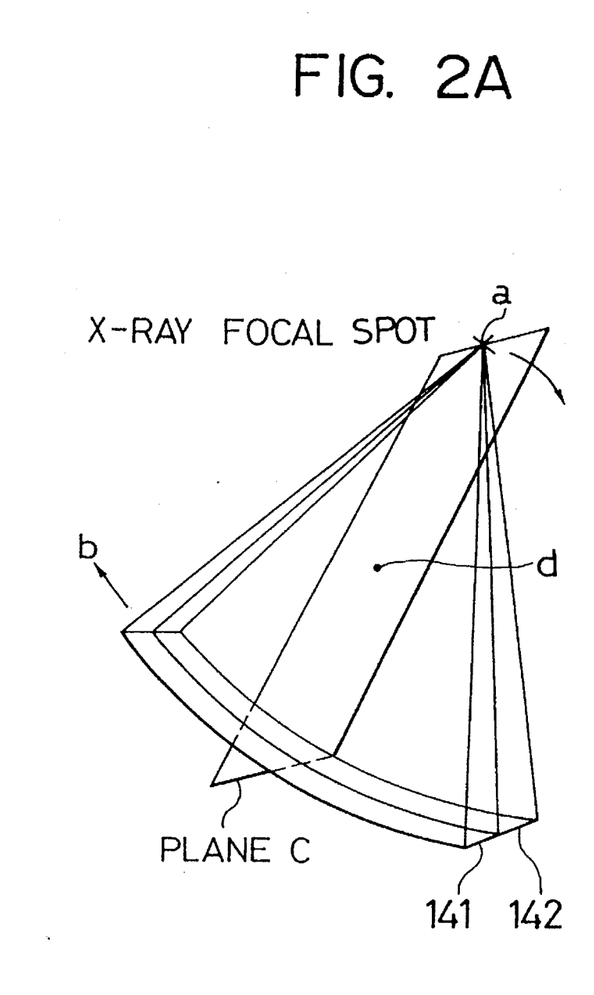
FIG. 2A shows detectors 141, 142 which rotate around the point d (rotation center) with an X-ray focal spot a in the direction b.
Figure 2B:
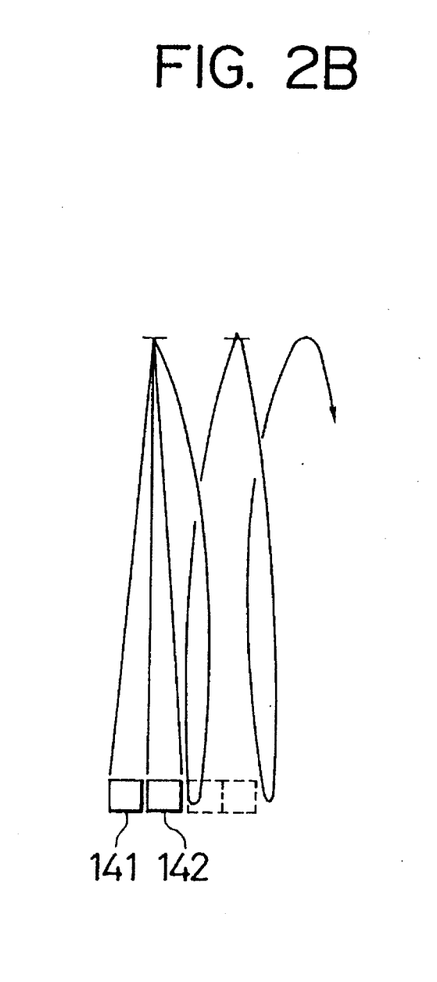
FIG. 2B is a cross sectional view taken along a plane c shown in FIG. 2A.
Figure 2C:
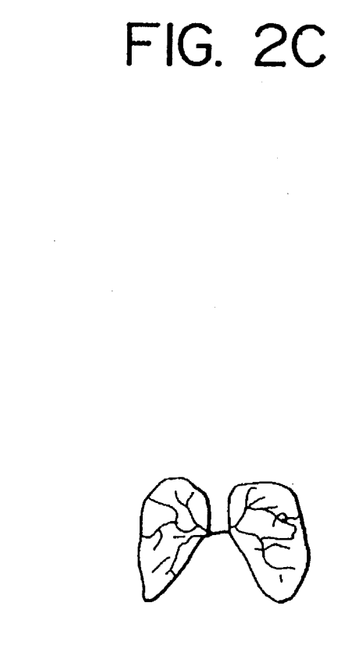
FIG. 2C is a reconstructed tomographic image.

FIGS. 2A–2C illustrates arrangement and locus of the detector in the double-slice CT apparatus according to the helical scanning system. FIG. 2A shows detectors 141, 142 which rotate around a point d (rotation center) with an X-ray focal spot a in the direction b. The characteristics for detectors 141, 142 are identical to each other, and the detector 141 is disposed right next to the detector 142. FIG. 2B is a cross sectional view taken along a plane c. In FIG. 2B, there are also shown the neighboring detectors 141 and 142, and a helical locus of the detectors with respect to a slice direction, accompanied by the rotation of the detectors and the movement of a bed portion (couch).

In the conventional double-slice CT apparatus, detecting methods for detecting the transmission X-ray quantity in the two detecting system are identical to each other. Thereby, speed at which the data are acquired is twice as a case where there is provided only a single detector, and resolution for the reconstructed tomographic images is improved over the case utilizing a single detector. However, as shown in FIG. 2C, the reconstructed tomographic image contains image data based on a single energy characteristic. Unlike $T_1$ (longitudinal magnetic relaxation time) and $T_2$ (transverse magnetic relaxation time) modes in a magnetic resonance imaging (MRI) apparatus, the tomographic image cannot be reconstructed from plural kinds of energy characteristics in the conventional practice.

SUMMARY OF THE INVENTION

In view of the foregoing drawbacks, it is therefore an object of the present invention to provide a computerized tomographic (CT) imaging apparatus which can achieve a multiple energy scanning system on a real time basis so that plural kinds of tomographic information can be obtained corresponding to plural types of energy characteristics.

To achieve the object, there is provided an X-ray CT imaging apparatus comprising: an X-ray tube for irradiating an X-ray to a biological body under medical examination; a plurality of detection systems for detecting an X-ray energy transmitted through the biological body, the plural detection systems having different energy characteristics respectively; data acquisition means for acquiring respective transmission X-ray energy data of the biological body which are detected by the plural detection systems; and reconstruction means for reconstructing a tomographic image for the biological body in accordance with data from the data acquisition means.

BRIEF DESCRIPTION OF THE DRAWINGS

These and other objects, features and advantages of the present invention will become more apparent from the following description of the preferred embodiment taken in conjunction with the accompanying drawings, in which.

DETAILED DESCRIPTION OF THE PREFERRED EMBODIMENTS

Features of the present invention will become apparent in the course of the following description of exemplary embodiments which are given for illustration of the invention and are not intended to be limiting thereof. Embodiments of the present invention will now be described with reference to the drawings.

Embodiment No. 1

Figure 3:
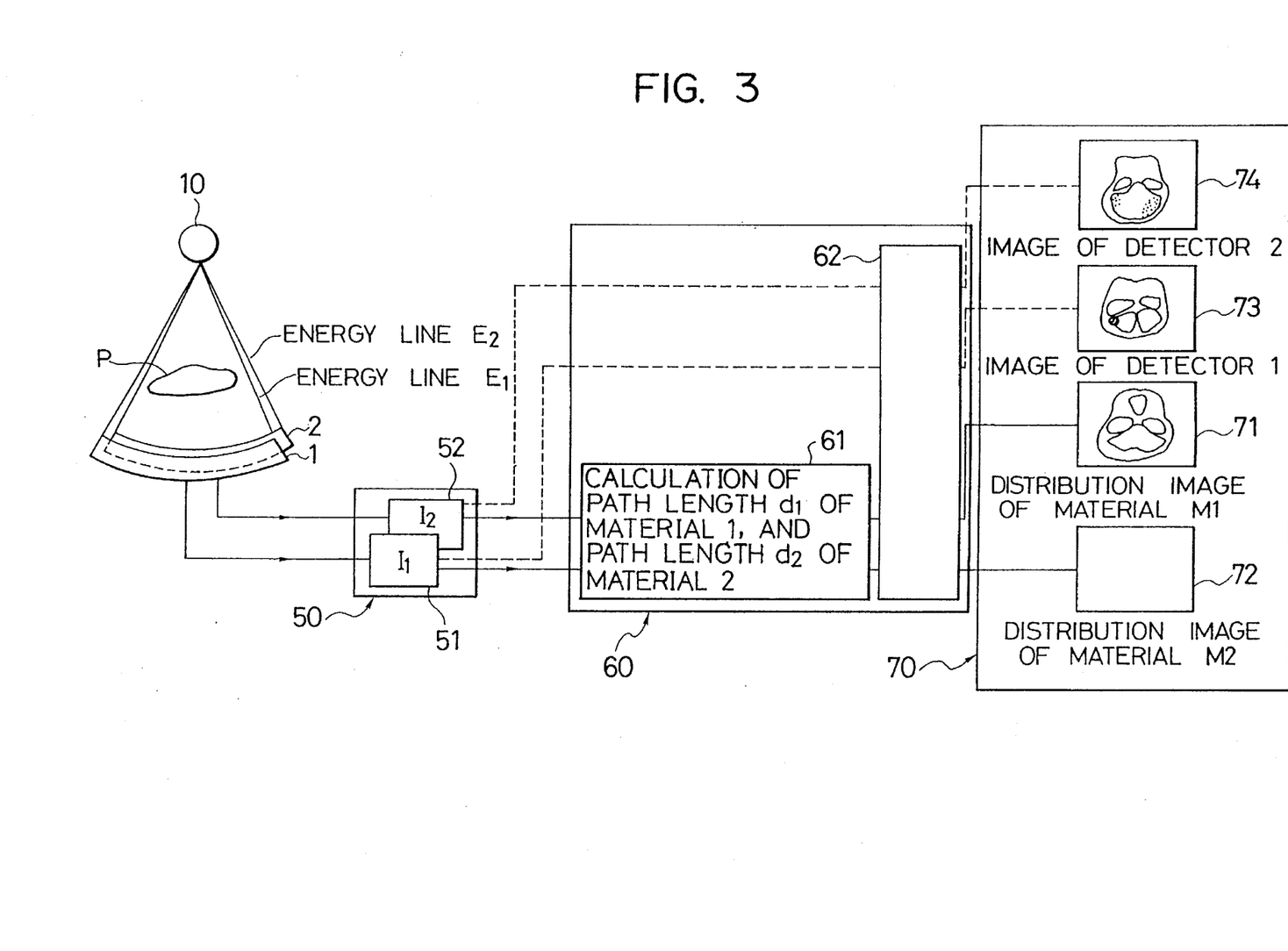
FIG. 3 is a block diagram showing a principle in construction of an X-ray CT (computerized tomographic) imaging apparatus utilizing a dual energy scanning technique according to a preferred embodiment serving as a multi-energy scanning type X-ray CT imaging apparatus.

FIG. 3 is a block diagram showing a principle in construction of an X-ray CT (computerized tomographic) imaging apparatus utilizing a dual energy scanning technique according to a preferred embodiment serving as a multi-energy scanning type X-ray CT imaging apparatus.

Referring to FIG. 3, the dual-energy scanning type X-ray CT apparatus comprises: an X-ray tube 10, detectors 1, 2 which detect respectively X-ray absorption amount of a biological body P under medical examination, a data acquisition portion 50 which acquires data regarding X-ray energy characteristics obtained by detectors 1, 2 and a translation amount of the biological body (that is to say, how much the body lying on a bed portion is moved), a reconstruction portion 60 in which a tomographic image of the body P is reconstructed based on data from the data acquisition portion 50, and a display unit 70 which displays the reconstructed tomographic image.

Most importantly, the detector 1 and the detector 2 are provided to detect different energy characteristics from each other.

Still referring to FIG. 3, the data acquisition portion 50 is comprised of an acquisition portion 51 which acquires data from the detector 1, and another acquisition portion 52 which acquires data from the detector 2.

The reconstruction portion 60 is constructed by an energy-distribution calculating portion 61 and an image reconstruction portion 62. In the energy-distribution calculating portion 61, path lengths d1, d2 for material M1, M2, respectively, are obtained in accordance with data from acquisition portions 51, 52 by following a predetermined calculation procedure which will be described hereinafter. In the image reconstruction portion 62, distribution images (tomographic images) for respective material M1, M2 are reconstructed from results of the energy-distribution calculating portion 60, and/or tomographic image data at respective detectors 1, 2 are reconstructed in accordance with acquired data respectively from the acquisition portions 51, 52.

In FIG. 3, an image 71 is an example of a distribution image of material M1, and an image 72 is an example of the distribution image of material M2. An image 73 is an example of the tomographic image detected by the detector 1, and an image 74 is an example of the tomographic image detected by the detector 2. These plural images are displayed on a single display screen by use of a multi-display method (multi-display) or a window display method (window display). Alternatively, these images may be displayed one by one by use of a single-image switching display method and the like.

The following equations (1) and (2) represent exemplary calculation procedures taken in the energy-distribution calculating portion 61 to obtain path lengths d1, d2 for material M1, M2, respectively.

$$I_1 = k \cdot \int \phi_1(E) \exp(-\mu_1(E) \cdot d_1 - \mu_2(E) d_2) dE \quad (1)$$

$$I_2 = \int \phi_2(E) \exp(-\mu_1(E) \cdot d_1 - \mu_2(E) d_2) dE \quad (2)$$

where $I_1$ and $I_2$ are outputs of the detectors 1, 2, respectively, and $\mu_1$ and $\mu_2$ are X-ray absorption factors for material M1 and M2, respectively.

Now, it is presupposed that every linear absorption coefficient $\mu$ is expressed by a linear combination of two predetermined absorption coefficients of two differnt types of material, as shown in equation (3). In other words, an X-ray linear absorption coefficient $\mu_o(E)$ of energy E for a certain material can be expressed by linear combination of linear absorption coefficients of two different materials. Note that the subscript $_o$ indicates a certain object so that $\mu_o(E)$ means the linear absorption coefficient of energy E for a certain material.

$$\mu_o(E) = \alpha \cdot \mu_1(E) + \beta \cdot \mu_2(E) \quad (3)$$

Now, let us describe a principle regarding relation between an X-ray amount energy that irradiates into the biological body, an X-ray amount energy that permeates (penetrates) through the biological body, and an X-ray amount that is absorbed in the detector. $\psi_1(E)$ is defined to be the X-ray amount energy that is irradiated from an X-ray tube (X-ray source). If a vertical distance (length) from an upper end to a lower end in a cross section of the biological body is denoted as d and an linear absorption coefficient is $\mu_o$, the X-ray amount energy that penetrates through the biological body is represented by $\psi_1(E)\exp(-\mu_o(E)d_o)$. Moreover, an X-ray amount energy that has also penetrated through the detector is expressed by $\psi_1(E)\exp(-\mu_o(E)d_o)\exp(-\mu_{D1}(E)\cdot d_{D1})$. Therefore, the X-ray amount absorbed in the detector is expressed by $$\{\psi_1(E)\exp(-\mu_o(E)d_o)\} - \{\psi_1(E)\exp(-\mu_o(E)d_o)\exp(-\mu_{D1}(E)\cdot d_{D1})\} =$$
$$\psi_1(E)\exp(-\mu_o(E)d_o)\{1-\exp(-\mu_{D1}(E)\cdot d_{D1})\}$$

where $\mu_{D1}$ represents a detector $D_1$'s linear absorption coefficient, and $d_{D1}$ indicates a detector $D_1$'s depth. Then, $\psi_1(E)\{1-\exp(-\mu_{D1}(E)\cdot d_{D1})\}$ is defined to be $\phi_1(E)$. Now, $\exp(-\mu_o(E)d_o)$ can be replaced with $$\exp(-\mu_1(E)\cdot d_1 - \mu_2(E)\cdot d_2).$$

Though $\phi_2$ can be defined in a similar manner with $\phi_1$, $\psi i(E)$ or $\mu_{Di}(E)\cdot d_{Di}$ (i=1, 2) can be varied by the detector arrays 1, 2 in the dual-energy scanning system so that $\phi_1$ and $\phi_2$ can be varied.

The constant k appearing in equation (1) is inserted so as to have an X-ray dosage difference between the detectors 1 and 2. However, the constant k can be dropped therefrom if an equivalent quantity to k is included into the $\phi_1(E)$.

Moreover, in equations (1) and (2) a loss or the like is not considered which is caused in a process during which a signal is produced after the X-ray is absorbed in the detector. However, such a loss may be included into $\phi_1(E)$. Moreover, though it is assumed that the biological body to be examined presents a uniformly qualified material, it may be assumed otherwise. Let us illustrate such a nonuniform case below.

$\psi i(E)$ is defined to be the X-ray amount (energy) that is irradiated from the X-ray tube (X-ray source) to i-th side of detector arrays. An X-ray absorption coefficient for location x is defined to be $\mu_o(E, x)$. Then, the X-ray amount for the energy that penetrates through the biological body in the i-th side of the detector arrays is represented by $\psi_1(E)\cdot\exp(-\int\mu_o(E, x))dx)$. An X-ray amount that is absorbed by the detector situated at the i-th side of the detector arrays, is expressed by:

$$\psi_1(E)\cdot\exp(-\int\mu_o(E, x)dx)\cdot\pi i(E),$$

in which $\psi_1(E)\cdot\pi i(E)$ is defined to be $\phi i(E)$ and $\exp(-\int\mu_o(E, x)dx)$ can be replaced with $$\exp(-\mu_1(E)\cdot d_1 - \mu_2(E)\cdot d_2).$$

Figure 4A:
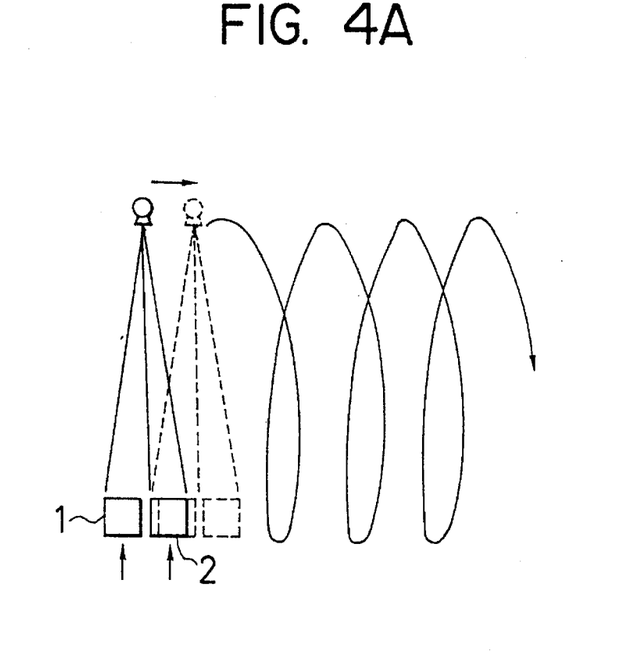
FIG. 4A shows cross sections of the detectors 1, 2 (whose energy characteristics are different from each other) and a helical-shape locus of the detector in the helical scanning system.
Figure 4B:
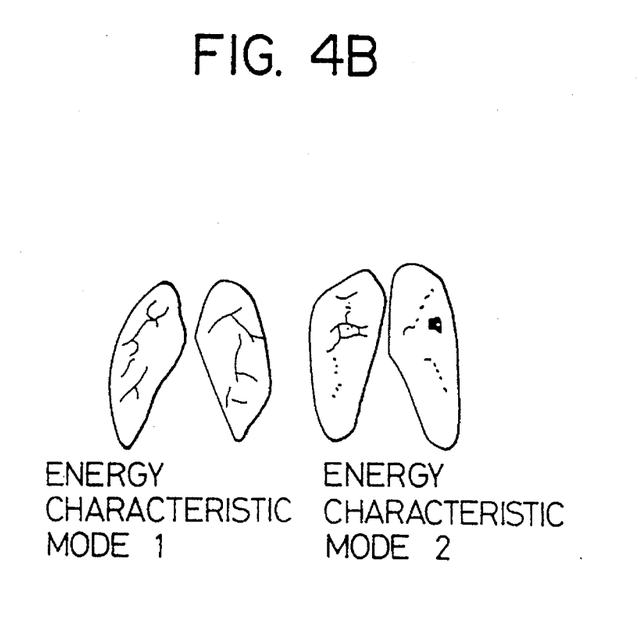
FIG. 4B shows two exemplary images having different energy characteristics where the left-hand image is obtained by using an energy characteristic 1, and the right-hand image is obtained by another energy characteristic mode 2.

FIG. 4A and FIG. 4B illustrates an example where the detectors each of which have a different energy characteristic from other. FIG. 4A shows cross sections of the detectors 1, 2 (whose energy characteristics are different from each other) and a helical-shape locus of the detector in the helical scanning system. It is to be noted that, referring still to FIG. 4A, when translation pitch of the bed portion in the longitudinal direction is set at one over an integral multiple of a pitch of the detector arrays in a detection system, the loci of two detection arrays are overlapped exactly.

The detectors 1, 2 have different energy characteristics from each other. In other words, the detector 1 detects the X-ray absorption characteristic for material M1, while the detector 2 detects one for material M2. Thereafter, the acquisition portions 51, 52 in the data acquisition portion 50 acquire data from the detectors 51, 52. Thereafter, in the energy-distribution calculating portion 61 of the reconstruction portion 60, the path lengths d1, d2 are obtained by a predetermined calculation technique, for example, by solving equations (1) and (2) in accordance with the data obtained from the acquisition portions 51, 52.

Moreover, in the image reconstruction portion 62, tomographic data are reconstructed based on a distribution image (tomographic image) for each material M1 and material M2 as a result of the energy-distribution calculating portion 61 and/or respective data from the acquisition portions 51, 52. Thereafter, the thus reconstructed data are stored in an image storing unit and is displayed on the display unit 70 via a display-processing system.

Further to equation (3), in general, the linear absorption coefficients differ for each portion of human body when the X-ray beam transverses (penetrates through) the human body. Now, there is raised a question as to how the integration $\int\mu_o(E, x)dx$ can be expressed. Now, by utilizing equation (3), taking integration of both sides of equation (3), there is obtained:

$$\int\mu_o(E, X) = \int\{\alpha(x)\mu_1(E) + \beta(x)\mu_2(E)\}dx$$
$$= (\int\alpha(x)dx)\mu_1(E) + (\int\beta(x)dx)\mu_2(E)\}$$

It is to be noted that $\int\alpha(x)dx$ corresponds to d1 and $\int\beta(x)dx$ corresponds to d2. Thus, in the nonuniform ease, the linear absorption coefficient can be expressed as the linear combination of $\mu_1(E) + \mu_2(E)$.

FIG. 4B shows two exemplary images having different energy characteristics where the left-hand image is obtained by using an energy characteristic mode 1, and the right-hand image is obtained by another energy characteristic mode 2.

Embodiment No. 2

The second embodiment is characterized in that as a detector there is utilized a solid detector comprised of a scintillator and a photodiode. Thus, each energy characteristic detected by each detector is differentiated from other, by varying a thickness of the scintillator in the solid detector.

Figure 5:
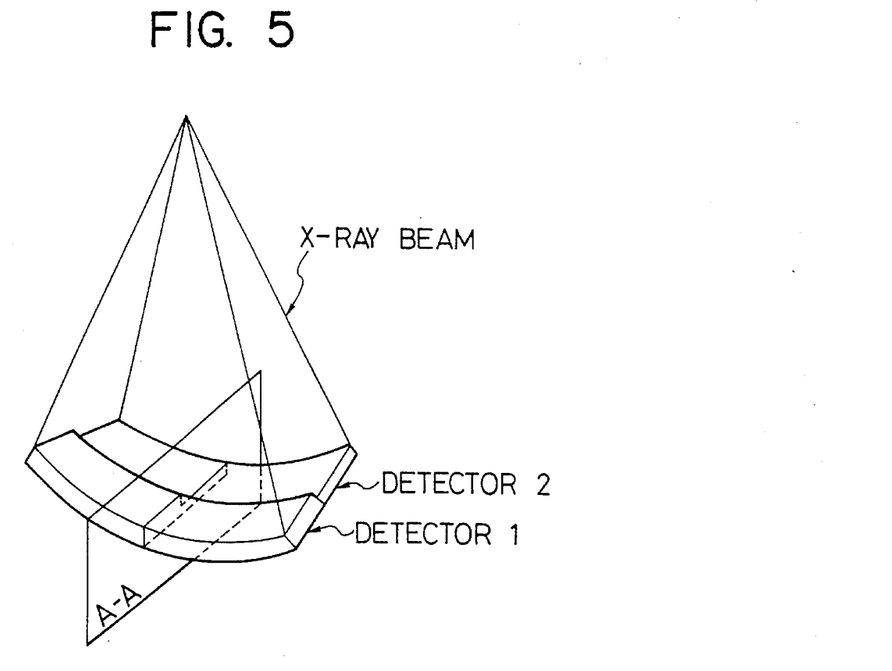
FIG. 5 is a perspective view showing a detection system where detectors having different thickness of the scintillators are used.
Figure 6:
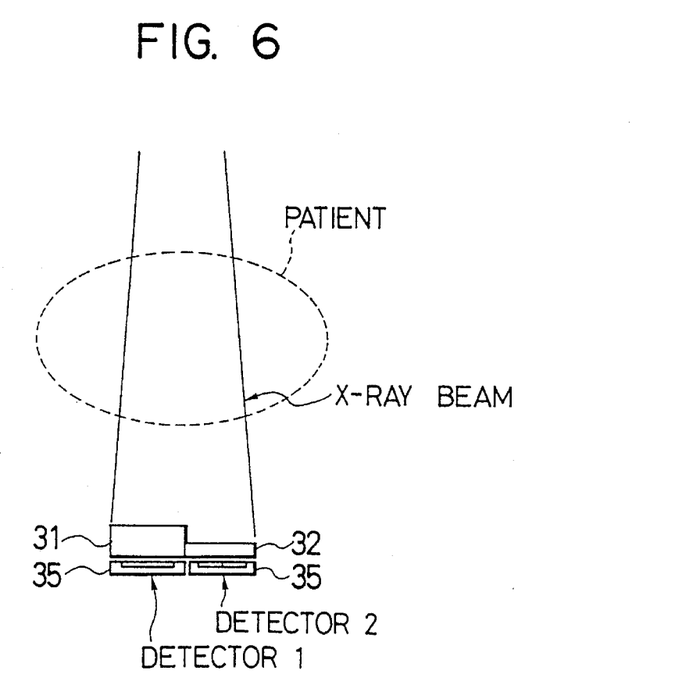
FIG. 6 is a cross sectional view substantially taken along line A—A shown in FIG. 5.
Figure 7:
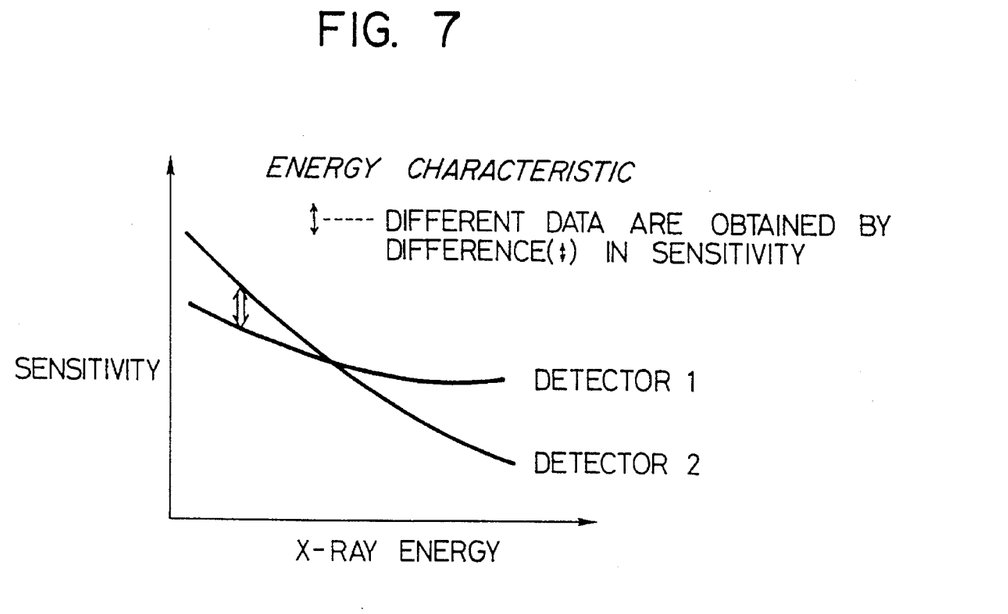
FIG. 7 is a graph showing distribution of energy characteristics for each detector.

FIG. 5 is a perspective view showing a detection system where detectors having different thickness of the scintillators are used. FIG. 6 is a cross sectional view substantially taken along line A—A shown in FIG. 5. FIG. 7 is a graph showing distribution of energy characteristics for each detector.

With reference to FIG. 6, the detection system is comprised of two types of detection series that are the detector 1 composed of a photodiode 35 and a scintillator 31, and the detector 2 composed of a photodiode 35 and a scintillator 32 whose thickness is smaller than that of the scintillator 31. In this case, as shown in FIG. 7, one of scintillators is made such that a thickness thereof is smaller (thinner) than other. Thus, the one of scintillators is designed to absorb only an X-ray beam whose energy is relatively low. On the other hand, the other of the scintillators is made such that a thickness thereof is greater (thicker) than the one described above. Thereby, the other one of scintillators is designed to have sensitivity for an X-ray beam whose energy is relatively high.

Accordingly, the energy characteristics of detectors 1, 2 are differentiated by differentiating the thickness of the scintillators from each other. In other words, energy sensitivity for the detector 2 is superior than in detector 1 in a case where the X-ray energy is relatively low; the energy sensitivity of the detector 1 is greater than in detector 2 in a case where the X-ray energy is relatively high.

As a variation for this second embodiment, it shall be appreciated that, on the detectors 1, 2, there may be provided filters whose X-ray absorption factors differ from each other. In this case of the variation, the thickness of both scintillators may be equal.

Embodiment No. 3

Figure 8:
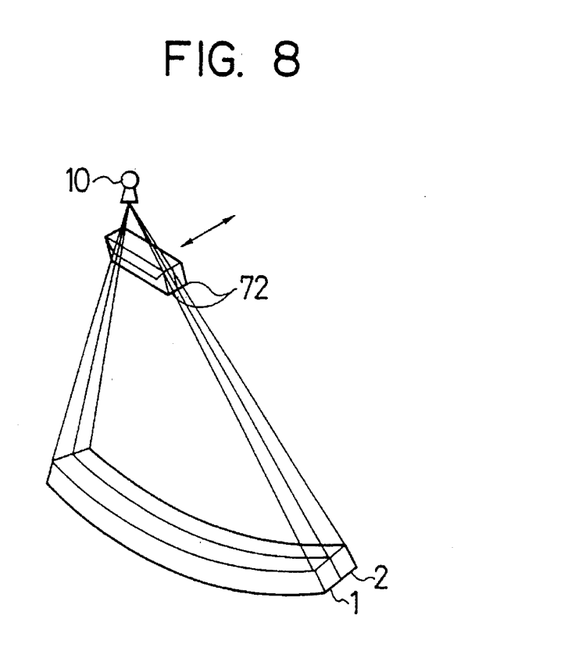
FIG. 8 is a perspective view of the detection systems where the thickness and/or material of the wedge differ from each other.

Referring to FIG. 8, the third embodiment is characterized in that the thickness, shape or material of a wedge provided in a close proximity of the X-ray tube 10 are differentiated for each detector. Thereby, the quality of radiation or the energy characteristics of the X-ray beams exposed to the biological body are differentiated in advance of being detected by the detectors. As a result thereof, the energy characteristics detected by each detector are differentiated.

Figure 9A:
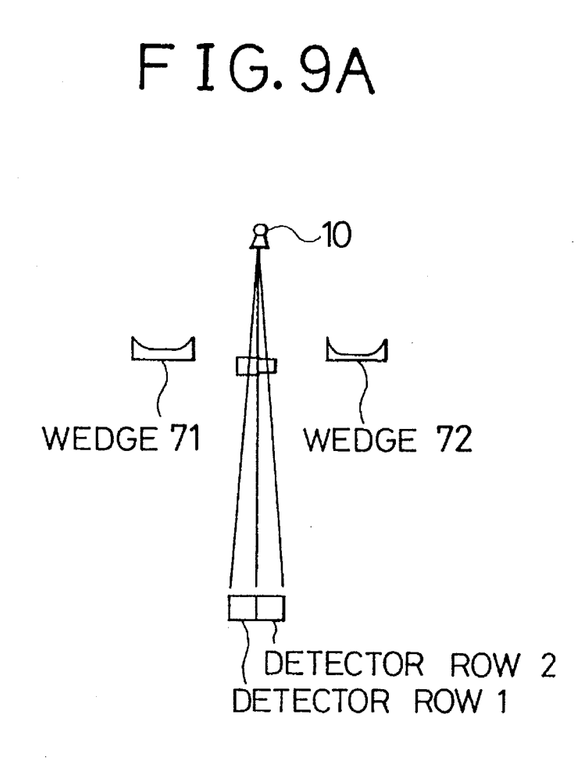
FIG. 9A is a cross sectional view of the wedge shown in FIG. 8.
Figure 9B:
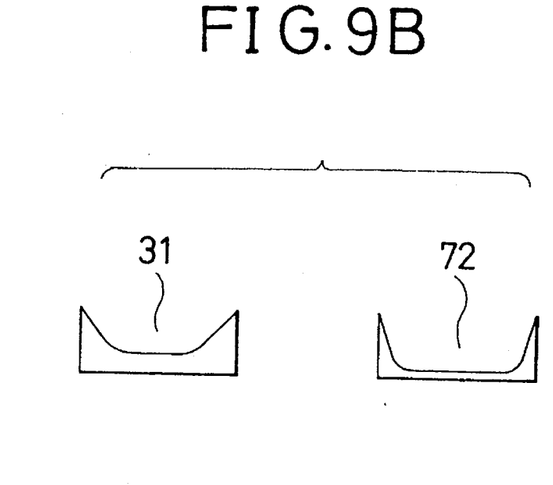
FIG. 9B shows two wedges each of which has different thickness from the other.
Figure 9C:
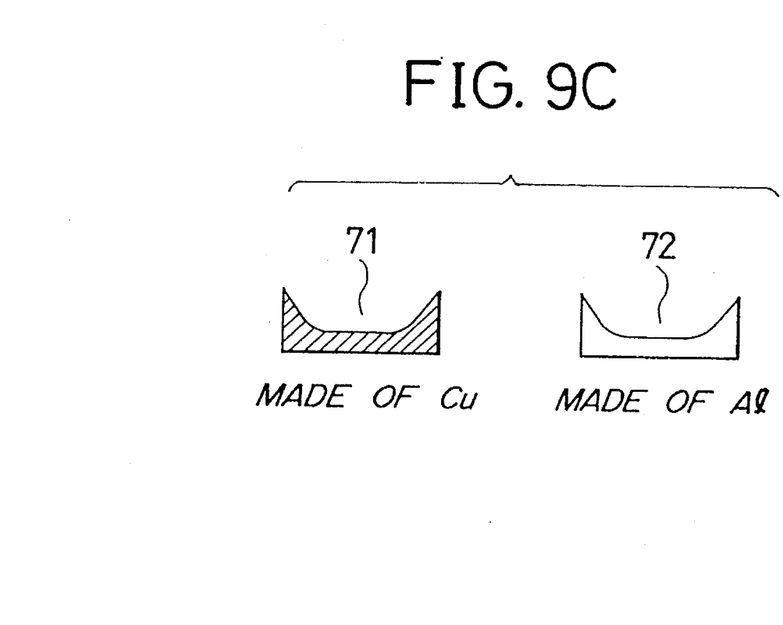
FIG. 9C shows another example where the material of the wedges is different from each other.
Figure 10:
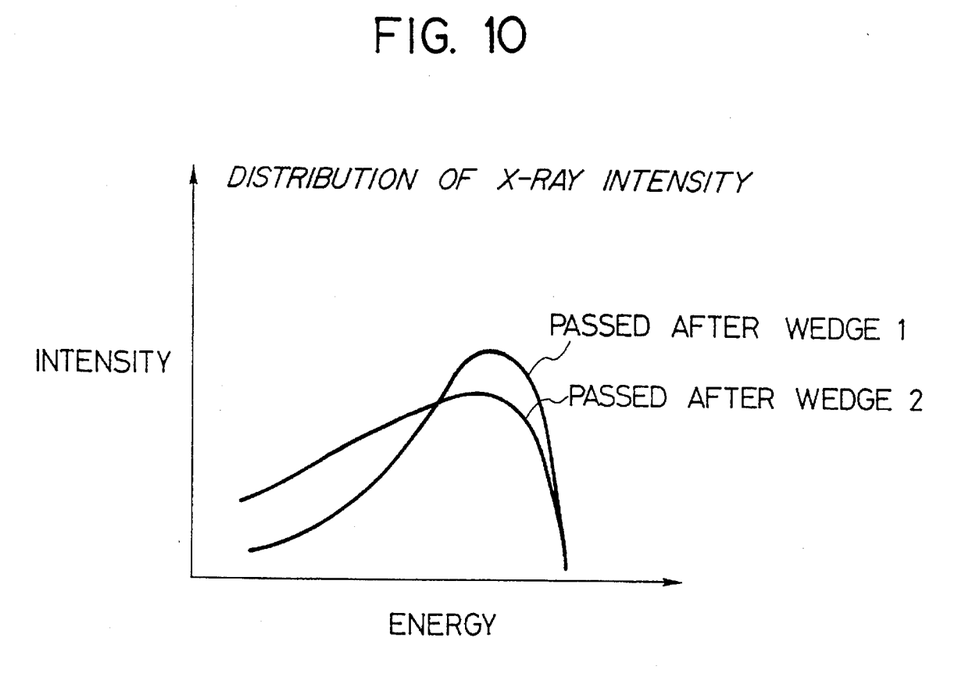
FIG. 10 is a graph showing distribution of the energy characteristics of the detection systems utilizing the wedges whose thickness and/or material differs from each other.

FIG. 8 is a perspective view of the detection systems where the thickness and/or material of the wedge differ from each other. FIG. 9A–FIG. 9C are cross sectional views of the wedge shown in FIG. 8. FIG. 10 is a graph showing distribution of the energy characteristics of the detection systems utilizing the wedges whose thickness and/or material differs from each other.

With reference to FIG. 8 and FIG. 9A, there are provided a wedge 71 and a wedge 72 corresponding to the detectors 1, 2, respectively. Though characteristics of the detectors 1, 2 are same to each other, the quality of the X-ray beams to be detected is different from each other. This is because the thickness or material is different in between the wedge 71 and the wedge 72, as shown in FIG. 9B and FIG. 9C.

FIG. 9B shows two wedges each of which has different thickness from the other. Since the thickness of the wedge 71 is greater (thicker) than that of the wedge 72, there is caused a difference of X-ray quality between the X-rays passing through the wedge 71 and the wedge 72. FIG. 9C shows another example where the material of the wedges is different from each other. In the example shown in FIG. 9C, the material of the wedge 71 is copper (Cu), while the material of the wedge 62 is aluminum (Al). Therefore, the X-ray passing through the wedge 71 differ, in the quality of radiation, from that passing through the wedge 62.

In this third embodiment, the detection system is comprised of two combination units. One combination unit is constituted by the wedge 71 and the detector 1, and other combination unit is constituted by the wedge 72 and the detector 2. Since the X-ray absorption factors differ in each combination unit from other, the energy characteristics of the detectors 1, 2 are differentiated from other detector, as shown in FIG. 10. Referring to FIG. 10, the detector 2 shows higher sensitivity in a portion where the X-ray energy is relatively low, whereas the detector 1 indicates higher sensitivity in a portion where the X-ray energy is relatively high.

Embodiment No. 4

The fourth embodiment is characterized in that an applied voltage (KV) for the X-ray tube 10 is differentiated. Thereby, the X-ray dosage irradiated from the X-ray tube 10 is differentiated for each detector, so that the energy characteristic detected by each detector is differentiated from one another.

Figure 11:
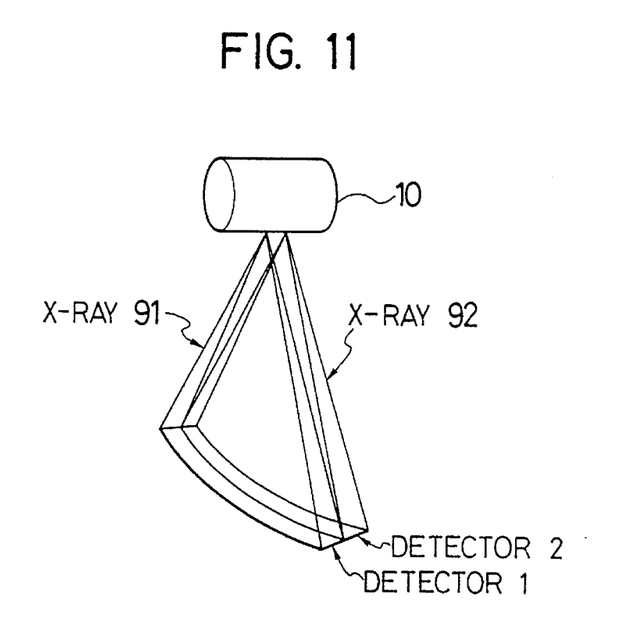
FIG. 11 is a perspective view showing detection systems utilizing different quality of X-ray beams.
Figure 12A:
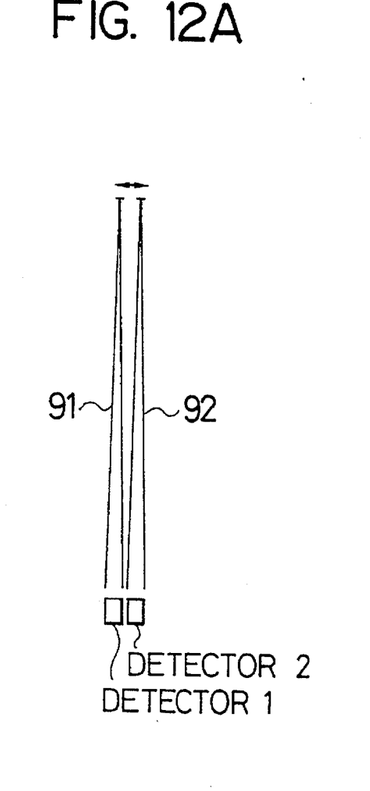
FIG. 12A–12C are cross sectional views of the detection systems shown in FIG. 11, and are provided to explain a method as to how to differentiate the applied voltage.
Figure 12B:
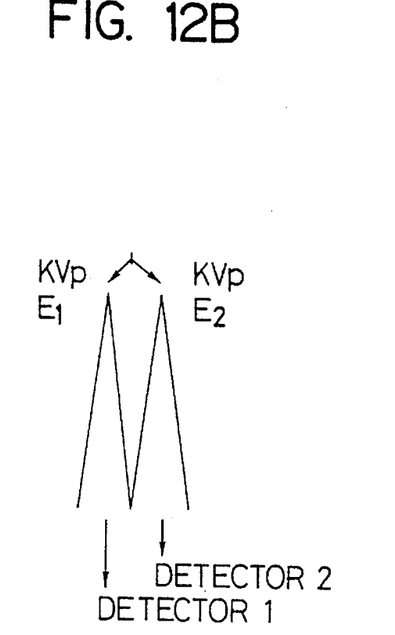
Figure 12C:
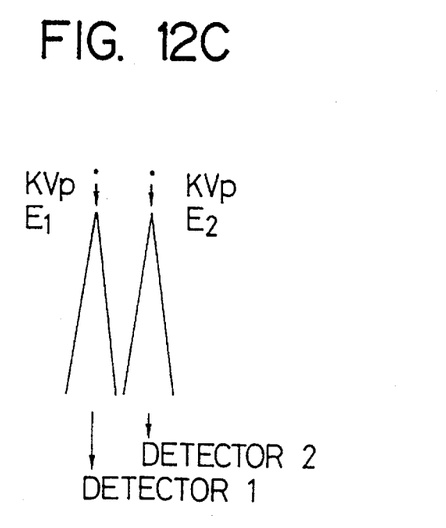
Figure 13:
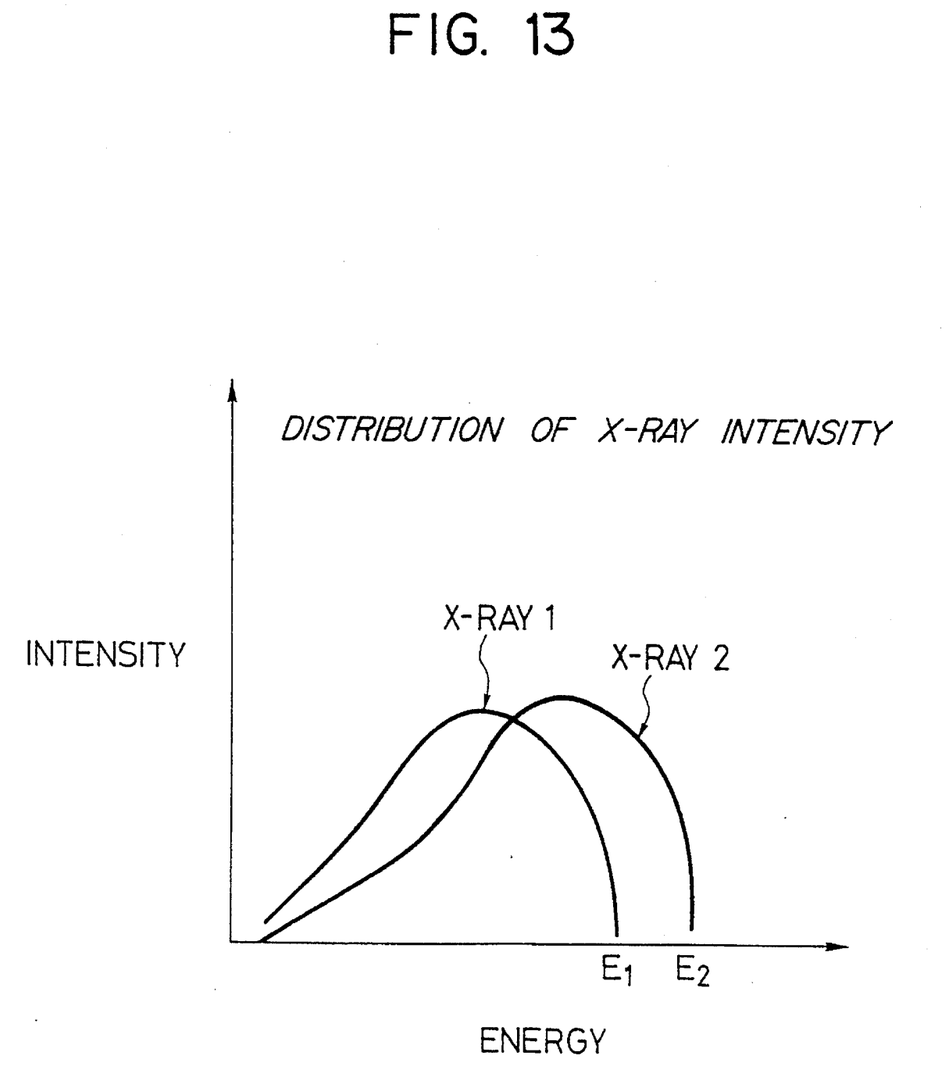
FIG. 13 is a graph showing distribution of the energy characteristics of the detection systems when the applied voltage is varied so that the X-ray spectrum corresponding to each detector is differentiated. See also FIG. 16 below for another example where the X-ray spectrum is altered.

FIG. 11 is a perspective view showing detection systems utilizing different quality of X-ray beams. FIG. 12A–12C are cross sectional views of the detection systems shown in FIG. 11, and are provided to explain a method as to how to differentiate the applied voltage. FIG. 13 is a graph showing distribution of the energy characteristics of the detection systems when the applied voltage is varied so that the X-ray amount corresponding to each detector is differentiated.

It is to be noted that the applied voltage for the X-ray tube 10 can, in general, be varied in a manner that a high-voltage generating apparatus is driven by a high-voltage control system (not shown) based on a controlling state of a main control system (not shown) in the X-ray CT imaging system.

Referring to FIG. 11 and FIG. 12A, X-ray 91 and X-ray 92 each of radiation spectrum (characteristic) differs from other are irradiated from the X-ray tube 10. Though the characteristics of both detectors 1, 2 are same, the radiation spectrums (characteristics) for the X-ray 91 and X-ray 92 differ respectively. Thereby, the absorption characteristics for each X-ray transmitted through the biological body P are different from each other.

FIG. 12B and FIG. 12C illustrate techniques as to how to differentiate the applied voltage. FIG. 12B shows an example where the X-ray tube 10 whose focal spot is swung in the direction of the detector arrays corresponding to the detectors 1, 2 by employing a flying focal spot method; then, an applied voltage KVp is switched for the detection arrays on demand, so that a voltage E1 and a voltage E2 which is different from E1 are produced.

For example, 80 KV is applied to detection array 1, and 140 KV is applied to detection array 2. Then, the focal spot is scanned in a manner that the focal spot is swung by employing the flying focal spot method, so that the quality of radiation is differentiated. The flying focal spot method is one of focal spot changing methods, and the focal spot is changed due to a change in a magnetic field in the X-ray tube 10.

FIG. 12C shows a case where there are provided two distinct focal spots for the X-ray tube 10 and the applied voltage therefor is differentiated from each other. Thereby, the applied voltages KVp of the X-ray tube 10 are produced as different voltages E1 and E2, corresponding to the detectors 1, 2.

Referring to FIG. 12A, the detection system is comprised of two distinct combinations, where one is composed of the X-ray 91 and the detector 1, and other is composed of the X-ray 92 and the detector 2. Since the X-ray amounts and characteristics differ as described above, the energy characteristics detected by the detectors 1, 2 differ from each other, as shown in FIG. 13. Namely, when the kVp of X-ray 92 is set to be greater than that of X-ray 91, the sensitivity of the detector 1 is greater for a portion where the X-ray energy is low, whereas the sensitivity of the detector 2 is superior for a portion where the X-ray energy is high.

Other Modifications

Besides the previously described embodiments No. 1 through No. 4, there can be considered other modified examples thereto as described below.

Figures 14A, 14B:
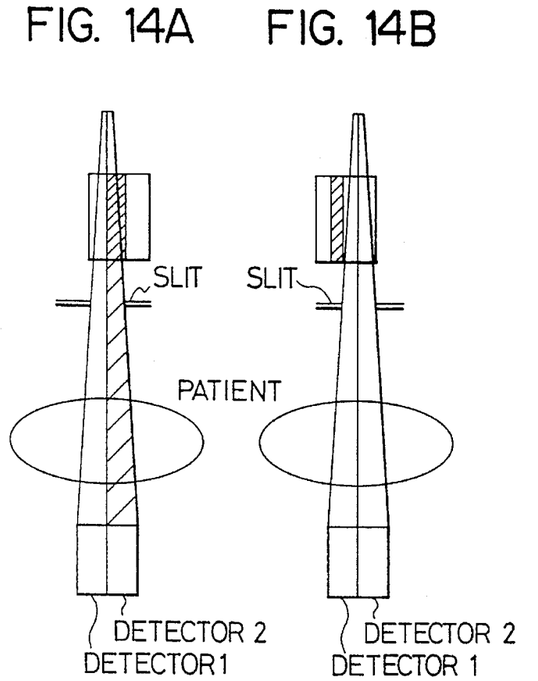
FIG. 14A and FIG. 14B show still another preferred embodiment where the X-ray beam passes through a wedge shown as a left-half portion of the wedge shown in FIG. 14A, when used with the dual-energy scanning operation; the X-ray beam passes through a wedge shown as a right-half portion of the wedge shown in FIG. 14B, when used with the multi-slice scanning operation.
Figures 15A, 15B:
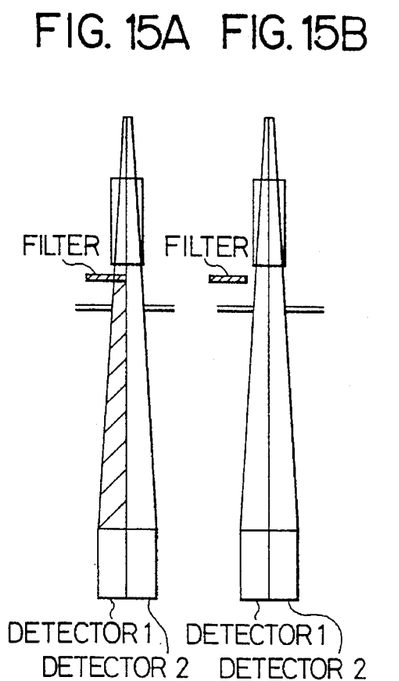
FIG. 15A and FIG. 15B show a modified embodiment to the embodiment shown in FIGS. 14A and 14B where the filter is in use at the time of the dual-energy scanning operation, whereas the filter is not in use at the time of multi-slice scanning operation.

It shall be appreciated that, as shown in FIGS. 14A and 14B, there may be provided a switching means for switching between for use with the dual-energy scanning operation (FIG. 14A) and the multi-slice scanning operation (FIG. 14B). In other words, the X-ray beam passes through a wedge shown as a left-half portion of the wedge shown in FIG. 14A, when used with the dual-energy scanning operation. The X-ray beam passes through a wedge shown as a right-half portion of the wedge shown in FIG. 14B, when used with the multi-slice scanning operation. Alternatively, there may be provided a filter as shown in FIG. 15A and FIG. 15B. In this case, the material for the wedge is preferably the same for both sides (dual-energy use and multi-slicing use).

Referring to FIG. 15A, the filter is in use at the time of the dual-energy scanning operation, whereas the filter is not in use at the time of multi-slice scanning operation. The examples shown in FIGS. 14A–15B can be more preferred to the second embodiment shown in FIG. 6 in a sense that, as shown in FIGS. 8–15B, a patient is not subject to unnecessary exposure of radiation compared to the second embodiment.

Figure 16:
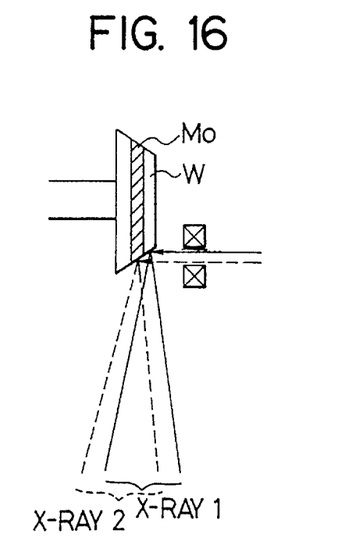
FIG. 16 shows still another preferred embodiment where there is provided a target which is comprised of plural kinds of material such as molybdenum (Mo) and tungsten (W) in order to alter an X-ray generating spectrum. See also FIG. 13. Both FIGS. 13 and 16 refer to how to differentiate the X-ray generating spectrum.

Moreover, with reference to FIG. 16, there may be provided a target or anode which is comprised of plural kinds of material such as molybdenum (Mo) and tungsten (W) in order to alter an X-ray generating spectrum.

Figure 17:
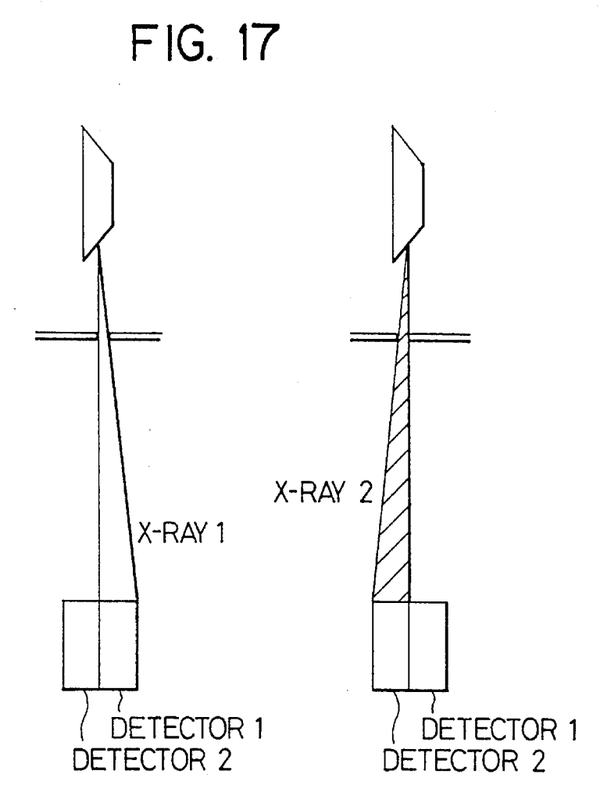
FIG. 17 shows still another preferred embodiment where there is provided an X-ray cut mechanism.
Figure 18:
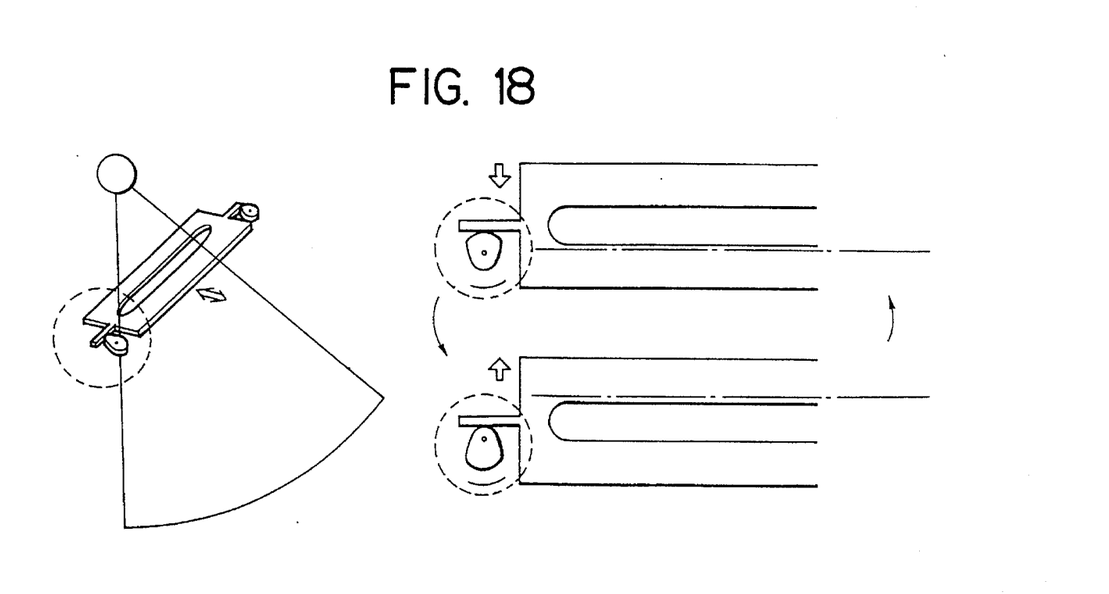
FIG. 18 illustrates how to cut off the X-ray according to the cut mechanism shown in FIG. 17.

Moreover, with reference to FIG. 17 and FIG. 18, there may be provided an X-ray cut mechanism. In the X-ray cut mechanism, the energy level is differentiated so that the X-ray entering to other half-side detector is shut off on demand. FIG. 18 illustrates an example of the X-ray cut mechanism shown in FIG. 17 where a position of a slit is changed by movement of a cam portion (indicated with a dotted line) which interlocks with a projected member of the slit. When the energy characteristics are varied by changing the kV of the X-ray beam, the patient will not receive unnecessary radiation.

Moreover, by combining above-described constructions and the helical scanning apparatus, there can be achieved a dual-energy scanning apparatus operated on a real time basis. Thereby, there can be obtained a fine-resolution tomographic image in accordance with two distinct types of energy characteristics, as in a case of a magnetic resonance imaging (MRI) apparatus realizing $T_1$ (longitudinal magnetic relaxation time) and $T_2$ (transverse magnetic relaxation time) modes.

Though the detection systems are described as two distinct ones for the purpose of simplicity, the detection systems may be comprised of more than three so as to realize a multi-energy scanning operation on a real time basis. In the case of having more than three different detection systems, the detectors and data acquisition portions therefor are to be increased in number corresponding to the number of the detectors and the data acquisition portions. Then, in the energy-distribution calculating portion 61, for example, equation (1) may be modified to three sets of equations which are to be numerically solved to obtain path lengths d1, d2, d3 for material M1, M2, M3.

Moreover, though the data acquisition portion 50 consists of two acquisition portions for an illustrative purpose, it may be arranged that a single acquisition portion is provided so that the data from the detectors can be switched to be processed in the single acquisition portion. The above-described option may be adopted for a case where there are provided more than three different detectors.

In summary, by employing the X-ray CT imaging apparatus according to the present invention, the energy characteristics for the plural detection systems are varied, so that the multi-energy scanning is realized in a real time basis where the plural detectors detect differentiated energy levels. Thus, based on thus acquired data there are obtained plural types of tomographic images corresponding to plural classes of energy characteristics. Thereby, a disease which is rather hard to be correctly located, such as a tumor, can be detected as early as possible due to a significant resolution power realized by the present invention.

Thus, of course, by setting two distinct detection systems, the dual-energy scanning can be realized which obtains tomographic images based on two energy characteristics as in $T_1$ (longitudinal magnetic relaxation time) and $T_2$ (transverse magnetic relaxation time) modes in the MRI apparatus.

Besides those already mentioned above, many modifications and variations of the above embodiments may be made without departing from the novel and advantageous features of the present invention. Accordingly, all such modifications and variations are intended to be included within the scope of the appended claims.

What is claimed is:

1. An X-ray computerized tomographic (CT) imaging apparatus comprising:

an X-ray tube for irradiating X-rays to a biological body under medical examination;

a plurality of detection systems for detecting an X-ray energy transmitted through the biological body, the plural detection systems having different energy characteristics respectively;

data acquisition means for acquiring respective transmission X-ray energy data of the biological body which are detected by the plural detection systems;

reconstruction means for reconstructing a tomographic image for the biological body in accordance with data from the data acquisition means; and switch means for switching between a dual-energy scanning mode and a multi-slice scanning mode.

2. The apparatus of claim 1, wherein the switch means includes an X-ray cutting means in which an energy level is differentiated among the plurality of detection systems.

3. A helical scanning type X-ray (CT) apparatus comprising:

X-ray source means for irradiating X-rays to a biological body, the X-ray source means rotating around the biological body;

a plurality of detection systems for detecting an X-ray energy transmitted through the biological body, the plural detection systems having different energy characteristics respectively;

a bed portion on which the biological body lies and which translates the biological body in a longitudinal direction;

bed drive means for driving the bed portion;

data acquisition means for acquiring respective transmission X-ray energy data of the biological body which are detected by the plural detection systems, and for acquiring translation data on the biological body lying on the bed portion;

reconstruction means for reconstructing a tomographic image for the biological body in accordance with data from the data acquisition means; and switch means for switching between a dual-energy scanning mode and a multi-slice scanning mode.

4. The apparatus of claim 3, wherein the switch means includes an X-ray cutting means in which an energy level is differentiated among the plurality of detection systems.

* * * * *